(12) United States Patent
Pagel et al.

(10) Patent No.: US 7,842,280 B2
(45) Date of Patent: Nov. 30, 2010

(54) FLEXIBLY LABELING PEPTIDES

(75) Inventors: Mark D. Pagel, Shaker Heights, OH (US); Byunghee Yoo, Mayfield Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 264 days.

(21) Appl. No.: 11/895,310

(22) Filed: Aug. 24, 2007

(65) Prior Publication Data

US 2008/0089842 A1 Apr. 17, 2008

Related U.S. Application Data

(60) Provisional application No. 60/842,687, filed on Sep. 6, 2006.

(51) Int. Cl.
*A61K 49/00* (2006.01)
*A61K 38/04* (2006.01)
*A61K 38/06* (2006.01)
*C07K 17/00* (2006.01)

(52) U.S. Cl. .................. 424/9.1; 530/324; 530/326; 530/328; 530/329; 530/330; 530/331

(58) Field of Classification Search .................. None
See application file for complete search history.

(56) References Cited

U.S. PATENT DOCUMENTS

2006/0039859 A1* 2/2006 Sharma et al. ............. 424/1.49

OTHER PUBLICATIONS

Smith et al. Radiochemical investigations of 177Lu-DOTA-8-Aoc-BBN[7-14]NH2: an in vitro / in vivo assessment of the targeting ability of this new radiopharmaceutical for PC-3 human prostate cancer cells. Nuclear Medicine and Biology. 2003. vol. 30, pp. 101-109.*

Yoo et al. A facile synthesis of alpha-amino-DOTA as a versatile molecular imaging probe. Tetrahedron Letters. 2006. vol. 47, pp. 7327-7330.*

De Leon-Rodriguez et al. The Synthesis and Chelation Chemistry of DOTA-Peptide Conjugates. Feb. 2008. vol. 19, No. 2, pp. 391-402.*

* cited by examiner

*Primary Examiner*—Marcela M Cordero Garcia
(74) *Attorney, Agent, or Firm*—McDonald Hopkins LLC

(57) ABSTRACT

A solid phase peptide synthesis method for synthesizing a peptidyl contrast agent is disclosed. In one example, the method includes synthesizing an amino-chelator loaded resin, coupling of the amino-chelator loaded resin to the C-terminus and/or backbone of a peptide, cleaving the amino-chelator-peptide from a resin, and chelating a lanthanide metal to the amino-chelator-peptide.

26 Claims, 6 Drawing Sheets

SEQUENCE LISTING

```
<160> NUMBER OF SEQ ID NOS: 16

<210> SEQ ID NO 1
<211> LENGTH: 4
<212> TYPE: PRT
<213> ORGANISM: Homo sapiens

<400> SEQUENCE: 1

Asp Glu Val Asp
1

<210> SEQ ID NO 2
<211> LENGTH: 7
<212> TYPE: PRT
```

```
<213> ORGANISM: Homo sapiens

<400> SEQUENCE: 2

Pro Leu Gly Met Trp Ser Gly
1               5

<210> SEQ ID NO 3
<211> LENGTH: 9
<212> TYPE: PRT
<213> ORGANISM: Homo sapiens

<400> SEQUENCE: 3

Cys Glu Leu Gly Ala Gln Leu Gln Cys
1               5

<210> SEQ ID NO 4
<211> LENGTH: 9
<212> TYPE: PRT
<213> ORGANISM: Homo sapiens

<400> SEQUENCE: 4

Cys Gly Glu Leu Gln Gln Ala Leu Cys
1               5

<210> SEQ ID NO 5
<211> LENGTH: 34
<212> TYPE: PRT
<213> ORGANISM: Homo sapiens

<400> SEQUENCE: 5

Gly Pro Arg Gly Pro Arg Gly Pro Arg Gly Pro Arg Gly Pro Arg
1               5                   10                  15

Gly Pro Arg Ser Ile Pro Pro Glu Val Lys Phe Asn Lys Pro Phe
                20                  25                  30

Val Tyr Leu Ile

<210> SEQ ID NO 6
<211> LENGTH: 16
<212> TYPE: PRT
<213> ORGANISM: Homo sapiens

<400> SEQUENCE: 6

Ser Ile Pro Pro Glu Val Lys Phe Asn Lys Pro Phe
1               5                   10

Val Tyr Leu Ile
        15

<210> SEQ ID NO 7
<211> LENGTH: 18
<212> TYPE: PRT
<213> ORGANISM: Homo sapiens

<400> SEQUENCE: 7

Gly Gly Cys Gly Arg Lys Lys Arg Arg Glu Arg Arg Arg Lys Asp Glu
1               5                   10                  15

Val Asp

<210> SEQ ID NO 8
<211> LENGTH: 17
<212> TYPE: PRT
<213> ORGANISM: Homo sapiens

<400> SEQUENCE: 8
```

```
Gly Arg Lys Lys Arg Arg Glu Arg Arg Gly Tyr Lys Asp Glu Val
1               5                   10                  15

Asp

<210> SEQ ID NO 9
<211> LENGTH: 3
<212> TYPE: PRT
<213> ORGANISM: Homo sapiens

<400> SEQUENCE: 9

Thr Phe Gly
1

<210> SEQ ID NO 10
<211> LENGTH: 7
<212> TYPE: PRT
<213> ORGANISM: Homo sapiens

<400> SEQUENCE: 10

Pro Leu Gly Met Trp Ser Arg
1               5

<210> SEQ ID NO 11
<211> LENGTH: 10
<212> TYPE: PRT
<213> ORGANISM: Homo sapiens

<400> SEQUENCE: 11

Asp Asp Asp Pro Leu Gly Met Trp Ser Arg
1               5                   10

<210> SEQ ID NO 12
<211> LENGTH: 7
<212> TYPE: PRT
<213> ORGANISM: Homo sapiens

<400> SEQUENCE: 12

Pro Leu Gly Leu Leu Ala Ala
1               5

<210> SEQ ID NO 13
<211> LENGTH: 10
<212> TYPE: PRT
<213> ORGANISM: Homo sapiens

<400> SEQUENCE: 13

Ser Gly Ala Val Arg Trp Leu Leu Thr Ala
1               5                   10

<210> SEQ ID NO 14
<211> LENGTH: 4
<212> TYPE: PRT
<213> ORGANISM: Homo sapiens

<400> SEQUENCE: 14

Ala Ala Pro Val
1

<210> SEQ ID NO 15
<211> LENGTH: 4
<212> TYPE: PRT
<213> ORGANISM: Homo sapiens
<220> FEATURE:
<221> NAME/KEY: MOD_RES
```

-continued

```
<222> LOCATION: 4
<223> OTHER INFORMATION: Xaa represents norvaline

<400> SEQUENCE: 15

Ala Ala Pro Xaa
1

<210> SEQ ID NO 16
<211> LENGTH: 3
<212> TYPE: PRT
<213> ORGANISM: Homo sapiens

<400> SEQUENCE: 16

Glx Arg Arg
1
```

FLEXIBLY LABELING PEPTIDES

CROSS REFERENCE TO RELATED APPLICATION

This application claims the benefit of U.S. Provisional Application 60/842,687 filed Sep. 6, 2006, titled Flexibly Labeling Peptides, by the same inventors.

COPYRIGHT NOTICE

A portion of the disclosure of this patent document contains material subject to copyright protection. The copyright owner has no objection to the facsimile reproduction of the patent document or the patent disclosure as it appears in the Patent and Trademark Office patent file or records, but otherwise reserves all copyright rights whatsoever.

BACKGROUND

Macrocyclic metal chelates using 1,4,7,10-tetraazacyclododecane-N,N',N'',N'''-tetraacetic acid (DOTA) may be administered to patients and animals to create or enhance contrast in biomedical imaging studies. Examples include paramagnetic Gd(III)-DOTA for magnetic resonance imaging (MRI), radioactive Tc-DOTA for single photon emission computed tomography (SPECT), and fluorescent Eu(III)-DOTA for fluorescence imaging. DOTA provides flexibility for synthetic derivatization that can change the pharmacokinetics of a chelate in vivo. This facilitates providing additional imaging information about biological processes.

Metal-DOTA chelates have been conjugated to peptides to affect the pharmacokinetics of a metal-DOTA imaging agent in vivo. This facilitates acquiring additional information about biological processes at the molecular level. A variety of peptidyl ligands have been employed for these molecular imaging studies, including peptides that bind to specific cell surface receptors, peptides that penetrate cell membranes, peptides that nonspecifically interact with the extracellular matrix, and peptide homopolymers that alter renal clearance rates.

The carboxylates of DOTA have conventionally been conjugated to the tertiary amines of peptides, including the N-terminal amine, the side chain amine of lysine, and unnatural amine-derivatized amino acid residues (e.g., p-NH$_2$-phenylalanine). Other DOTA derivatives have been devised for conjugation to peptide amino groups, (e.g., succinimide DOTA derivatives) and isothiocyanato DOTA derivatives. However, coupling DOTA only to the N-terminus of a peptide amine can limit synthesis methodologies and may compromise the utility of the peptidly contrast agent for molecular imaging.

BRIEF DESCRIPTION OF THE DRAWINGS

The accompanying drawings, which are incorporated in and constitute a part of the specification, illustrate various example methods, and other embodiments of various aspects of the invention. It will be appreciated that the illustrated element boundaries (e.g., boxes, groups of boxes, or other shapes) in the figures represent one example of the boundaries. One of ordinary skill in the art will appreciate that in some embodiments one element may be designed as multiple elements, multiple elements may be designed as one element, an element shown as an internal component of another element may be implemented as an external component and vice versa, and so on. Furthermore, elements may not be drawn to scale.

DETAILED DESCRIPTION

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Molecular Imaging", as used herein, refers to the visualization, characterization and measurement of biological processes at the molecular and cellular levels in humans and other living systems. The techniques used for molecular imaging may include nuclear medicine, magnetic resonance imaging (MRI), magnetic resonance spectroscopy (MRS), and optical imaging. In one example, molecular imaging may be facilitated by an aminoDOTA-peptide contrast agent that creates or enhances differentiation between a cell expressing a normal level of caspase and a cell expressing an elevated level of caspase.

This application describes a product (e.g., peptide) and a method for synthesizing the product. The method includes synthesizing a peptide to include an imaging agent (e.g., metal-DOTA). The imaging agent may be coupled directly to the peptide backbone, may be coupled by any type of side chain, may be coupled to the C-terminus of the peptide, and may be coupled to the N-terminus of the peptide. In one example, the application describes a peptide synthesis method where an amine-derivatized DOTA (aminoDOTA) can be coupled to the carboxylates of peptides. In one example, the method linked an aminoDOTA to a resin for use in SPPS in order to synthesize peptide-DOTA imaging agents with DOTA coupled to the C-terminus of a peptide. While the example describes coupling an amino-DOTA to a peptide, it is to be appreciated that an amino-DOTA can be coupled to an amino acid during peptide synthesis. In different examples, the chemical synthesis method can be used in manual peptide synthesis and in automated peptide synthesis.

In one example, the method facilitates creating PARAmagnetic Chemical Exchange Saturation Transfer (PARACEST) imaging contrast agents. For example, the method facilitates placing amide groups in close proximity to a lanthanide ion to facilitate PARACEST imaging. Thus, the method facilitates creating peptide-based imaging probes.

The following describes an example method used to produce a peptide with an imaging agent (e.g., metal-DOTA) coupled at the locations described above.

Figure 1:
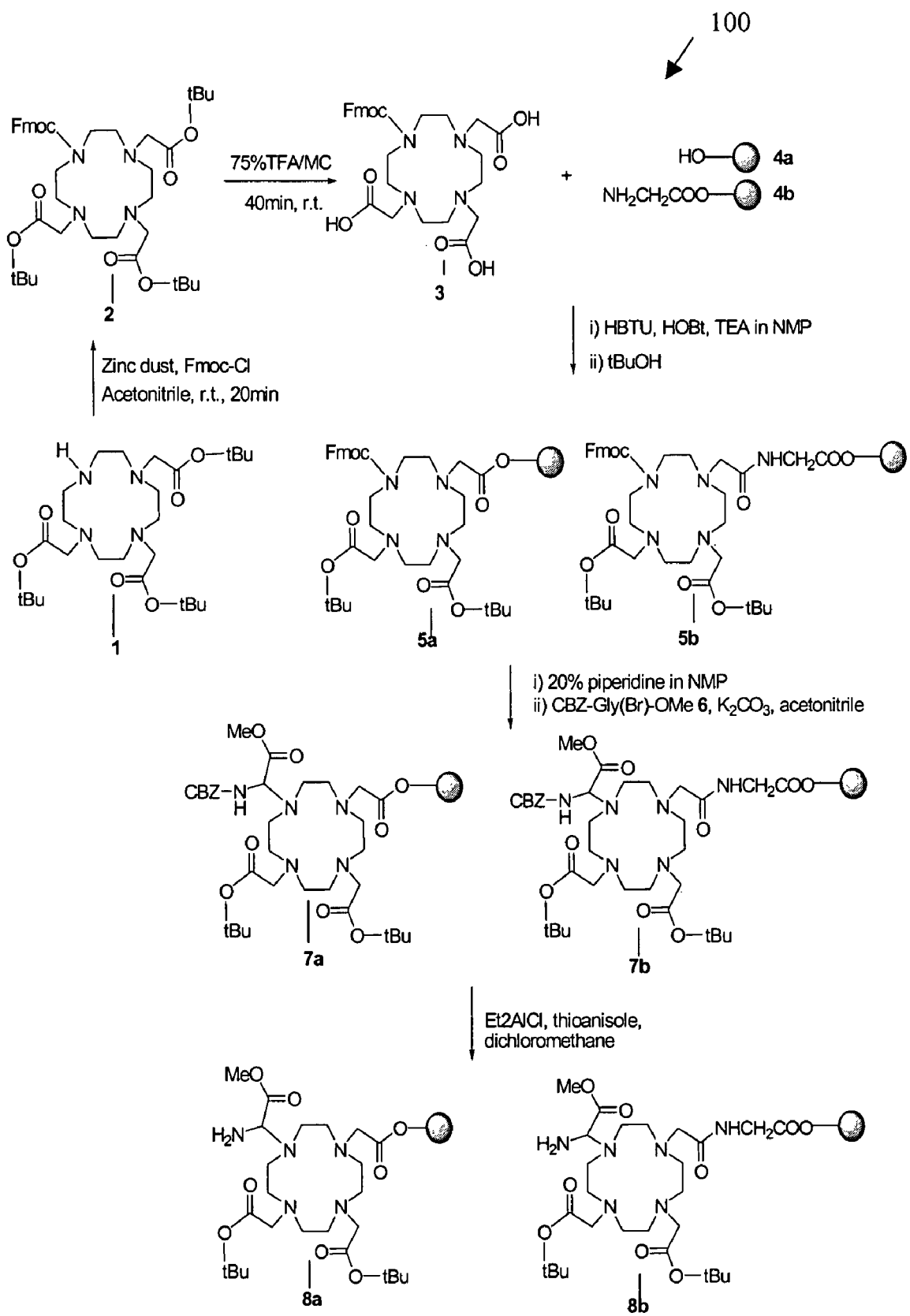
FIG. 1 illustrates an example synthesis strategy to create a DOTA-loaded resin for solid phase peptide synthesis (SPPS).

FIG. 1 illustrates an example synthesis strategy used to create a DOTA-loaded resin for solid phase peptide synthesis. 4,7,10-tri(t-butylacetate)-1-fluorenylmethoxycarbonyl-1,4,7,10-tetraazacyclododecane (Fmoc-DO3A-tBu)$_2$ was prepared by reacting 1,4,7,10-tetraazacyclododecane-N,N',N''-tri-(tert-butylacetate) (DO3A-tBu) 1 and Fmoc-Cl with activated Zn dust. While Fmoc was employed as the protecting group in the method described in FIG. 1, it is to be appreciated that other amine protecting groups may be employed in the synthesis of the DOTA loaded resin. Fmoc-DO3A-tBu 2 was treated with 75% TFA in MC for 40 minutes to remove tBu esters. The deprotected product was a complex of 4,7,10-tri(carboxymethyl)-1-fluorenylmethoxycarbonyl-1,4,7,10-tetraazacyclododecane (Fmoc-DO3A) 3 and TFA salt.

Compound 3 was coupled to a Wang resin 4a (sub.lev.=1.0 mmol/g) and a glycine-preloaded Wang resin 4b (sub. lev.=0.78 mmol/g) to create 5a and 5b, respectively. 5a and 5b showed 70% loading and 83% loading, respectively, as measured by quantitatively titrating the Fmoc group with a UV spectrometer operating at 301 nm wavelength. Adding an amino acid to the Wang resin lengthened the linker in 5b and led to improved loading efficiency. Compound 4b was prepared to demonstrate the incorporation of DOTA within a peptide sequence. In one example, a compound can be coupled to a resin using peptide coupling agents (e.g., HBTU, HOBt, HATU, HOAt). At the end of the coupling reaction to create 5a and 5b, an excess amount of t-BuOH was added to convert the remaining active carboxylates to tBu esters, and acetic anhydride was used to cap remaining functional active sites on the Wang resin.

While FIG. 1 only shows coupling of the Wang resin at position 1 and Fmoc protection at position 4 (or 10) of the cyclen ring it is to be appreciated that the Fmoc protection may also occur at position 7.

After the Fmoc groups of 5a and 5b were removed by 20% piperidine in NMP, 5a and 5b were coupled with α-brominated CBZ-Gly(Br)-OMe 13 to obtain 7a and 7b. The α-bromo glycine template 13 was produced as racemates at approximately a 1 to 1 ratio, which was indicated by the NMR doublet on 5.20 and 5.46 ppm. While piperidine is employed in the example synthesis described in FIG. 1, it is to be appreciated that other mild base treatments may be used to remove the Fmoc group.

The CBZ group may be used to orthogonally protect amine groups in organic syntheses. Cleavage of CBZ groups is conventionally performed with $H_2$/Pd—C or 1,4-cyclohexadiene/Pd—C in EtOH. However, these cleavage conditions are not compatible with SPPS using polymeric supports. Selective CBZ cleavage conditions were tested for SPPS. In one example, $BF_3.Et_2O$/dimethylthioether, trimethylsilyl iodide and $Et_2AlCl$/thioanisole conditions were investigated. The results of tracing the reactions for 7a and 7b with Kaiser's test, showed the strong Lewis acids $BF_3.Et_2O$/dimethylthioether and trimethylsilyl iodide were able to cleave the Wang linker on the resin, and therefore failed to selectively cleave the CBZ group. The CBZ group was found to be selectively cleaved with $Et_2AlCl$/thioanisole by reducing the temperature to −78° C. and by carefully controlling the reaction time and molar ratio of $Et_2AlCl$/thioanisole to optimize reaction conditions. The reaction rates were assessed by measuring the amine contents of ~25 mg of resin after the start of the reaction, by using a picric acid titration and a UV/Vis spectrometer operating at 358 nm. These results were compared to the measured Fmoc concentrations of 5a and 5b. To eliminate the effect of tertiary amines in the cyclen ring, the results of picric acid titration of 7a and 7b that were not subjected to $Et_2AlCl$/thioanisole was subtracted from the measurements of the cleavage reaction. Optimized conditions were determined to consist of a reaction time of 15 minutes at −78° C., 1 eq. of $Et_2AlCl$ and 2 eq. of thioanisole relative to the CBZ concentration on the resin. Under these conditions, cleavage of the benzyl ether group of the Wang linker or incomplete CBZ cleavage limited the overall yield of 8a and 8b to 70%.

Figure 2:
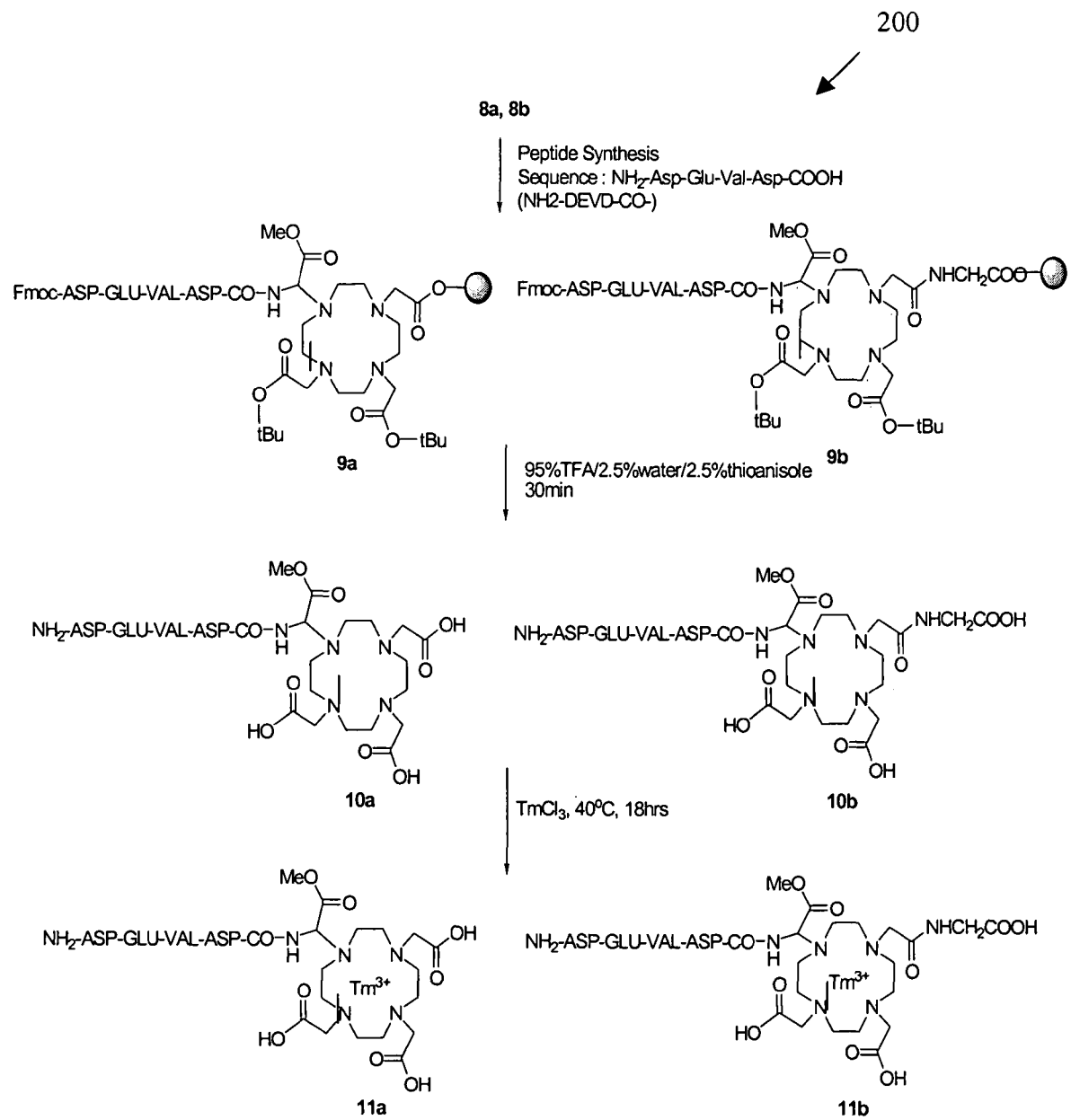
FIG. 2 illustrates an example method for step-wise coupling of amino acids to the aminoDOTA Wang resin using a SPPS method. The peptide Asp-Glu-Val-Asp corresponds to SEQ ID NO: 1.

FIG. 2 illustrates an example method for step-wise coupling of amino acids to the aminoDOTA Wang resin using a SPPS method. A peptide sequence (e.g., Asp-Glu-Val-Asp (SEQ ID NO: 1)) was chosen. In one example, the coupling efficiency was enhanced by applying two sequential applications of 4 equivalents of each amino acid to the SPPS after initial Fmoc deprotection. The total yield of step-wise SPPS of the four amino acids to amino-DOTA was 90% and 93% for the synthesis of 10a and 10b, respectively. This coupling efficiency indicates that the CBZ-protected amine is sufficiently exposed after deprotection, even in the presence of the bulky DOTA moiety. While a peptide with the sequence SEQ ID NO 1 (Asp-Glu-Val-Asp) was employed in the method detailed in FIG. 2, it is to be appreciated that other peptides may be employed. Table 1, as set forth below, provides examples of peptides that may be employed. A peptide that binds specifically to a cell surface receptor may be employed (e.g., SEQ ID Nos: 3 and 4). A peptide that penetrates a cell membrane may be employed (e.g., SEQ ID Nos: 5, 6, 7, and 8). A peptide that non-specifically interacts with the extracellular matrix may be employed. A peptide that alters renal clearance rates may be employed. A peptide capable of being covalently modified by an enzyme may be employed (e.g., SEQ ID Nos 1, 7, 8, 9, 11, 13, 14, 15, and 16). In one example, the peptide may be acetylated.

TABLE 1

| Peptide | Exemplary Purpose | Sequence |
|---|---|---|
| DEVD-DOTA | caspase-3 detection | SEQ ID NO: 1 |
| DEVD-DOTA-G | caspase-3 detection | |
| GGCGRKKRRQRRRKDEVD-DOTA | caspase-3 detection, intracellular delivery | SEQ ID NO: 7 |
| GRKKRRQRRRGYKDEVD-DOTA | caspase-3 detection, intracellular delivery | SEQ ID NO: 8 |

TABLE 1-continued

| Peptide | Exemplary Purpose | Sequence |
|---|---|---|
| TFG-DOTA | autophagin-1 detection | SEQ ID NO: 9 |
| ZRR-DOTA | Cathepsin B detection | SEQ ID NO: 16 |
| PLGMWSG-DOTA | MMP2/9 detection | |
| Ac-PLGMWSG-DOTA | MMP2/9 detection | SEQ ID NO: 2 |
| Ac-PLGMWSR-DOTA | MMP2/9 detection | SEQ ID NO: 10 |
| Ac-DDDPLGMWSR-DOTA | MMP2/9 detection | SEQ ID NO: 11 |
| Ac-PLGLLAA-DOTA | MMP2/9 detection | SEQ ID NO: 12 |
| SGAVRWLLTA-DOTA | MMP2/9 detection | SEQ ID NO: 13 |
| AAPV-DOTA | neutrophil elastase detection | SEQ ID NO: 14 |
| AAP-norvaline-DOTA | neutrophil elastase detection | SEQ ID NO: 15 |
| C-DOTA-SIPPEVKFNKPFVYLI | intracellular delivery (SPECT and MRI) | SEQ ID NO: 6 |
| C-DOTA-(GPR)$_6$-SIPPEVKFNKPFVYLI | intracellular delivery | SEQ ID NO: 5 |
| CELGAQLQC-DOTA | Targeting a cell surface receptor (SPECT) | SEQ ID NO: 3 |
| CGELQQALC-DOTA | Targeting a cell surface receptor (SPECT) | SEQ ID NO: 4 |

Products 9a and 9b were cleaved from the resin to produce 10a and 10b. These products were used to chelate Thullium ($Tm^{3+}$) using standard conjugation methods and an Arsenazo III color test to create 11a and 11b. While the method described in FIG. 2 illustrates Thuillium as the paramagnetic metal ion, other paramagnetic metal ions may be employed in the synthesis of an imaging agent linked to a peptide (e.g., $Eu^{3+}$, $Gd^{3+}$, $Yb^{3+}$).

In one example, PARACEST was used to demonstrate the application of the final products (e.g., 11a, 11b) of SPPS methods for molecular imaging. The PARACEST effect is created by saturating a unique NMR chemical shift corresponding to an amide hydrogen (or more generally, a hydrogen of a functional group that that exchanges with water at a rate of approximately 100-5000 sec-1), and the effect is detected by observing a decrease in the water signal caused by transferring the saturation through chemical exchange. This mechanism for detecting imaging contrast agents is useful in biomedical applications that use MRI. PARACEST exploits the close proximity between the amide group and the lanthanide ion to create a unique NMR chemical shift for the amide group of the imaging agent, which facilitates selective saturation of this chemical shift. In one example, the SPPS methods placed amide groups in close proximity to the lanthanide ion to facilitate PARACEST imaging.

Figure 3:
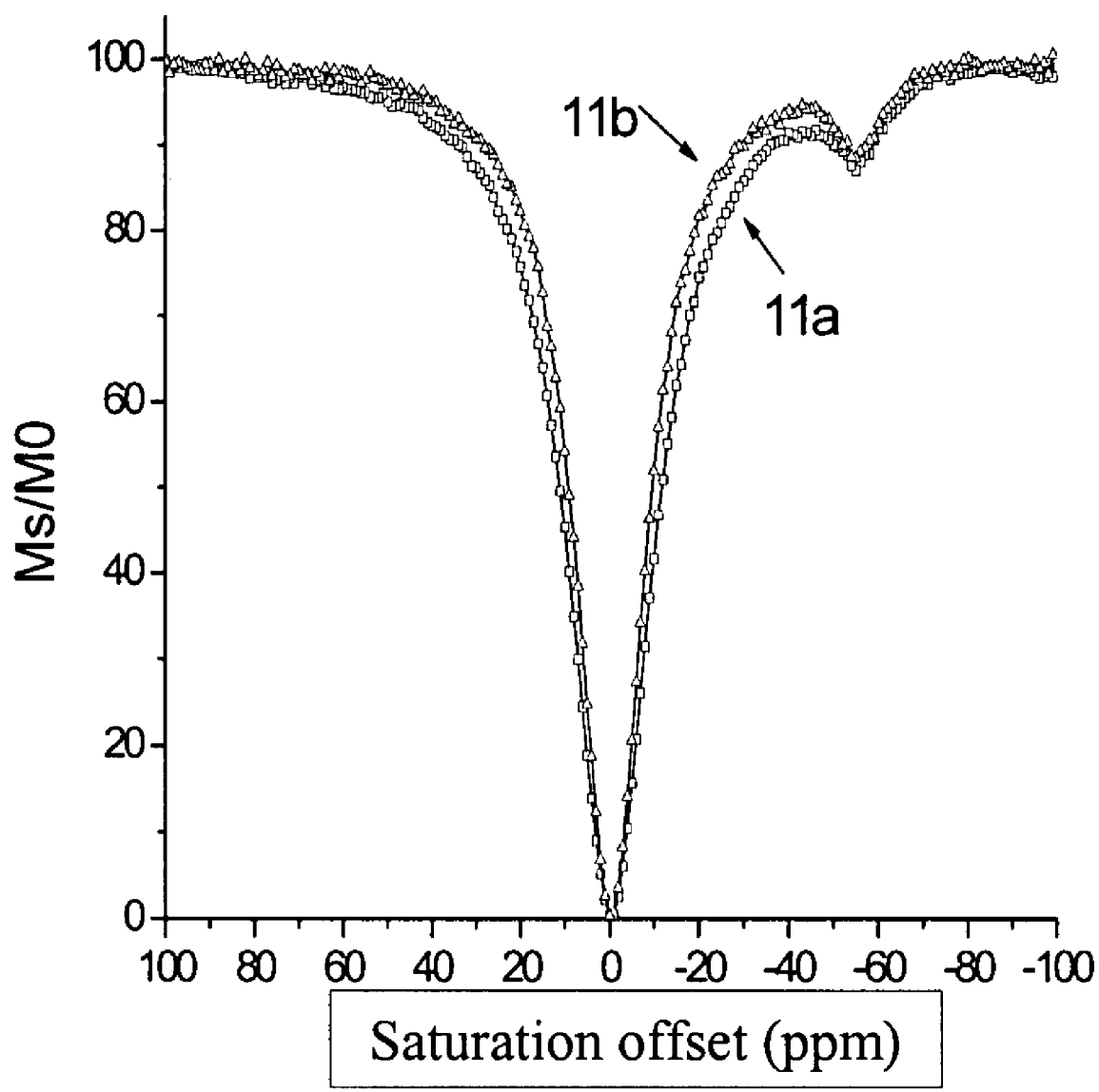
FIG. 3 illustrates PARACEST spectrums of synthesized imaging agents.

FIG. 3 illustrates the PARACEST spectrum of 11a (25 mM in 5% $D_2O$ in $H_2O$) and 11b (12 mM in 5% $D_2O$ in $H_2O$). PARACEST spectra were acquired using a Varian Inova 600 MHz NMR spectrometer with a modified presaturation pulse sequence that included a continuous wave saturation pulse, saturation pulse power of 31 μT, saturation delay of 4 seconds. The graph in FIG. 3 shows a PARACEST effect detected at −51 ppm.

Figure 4:
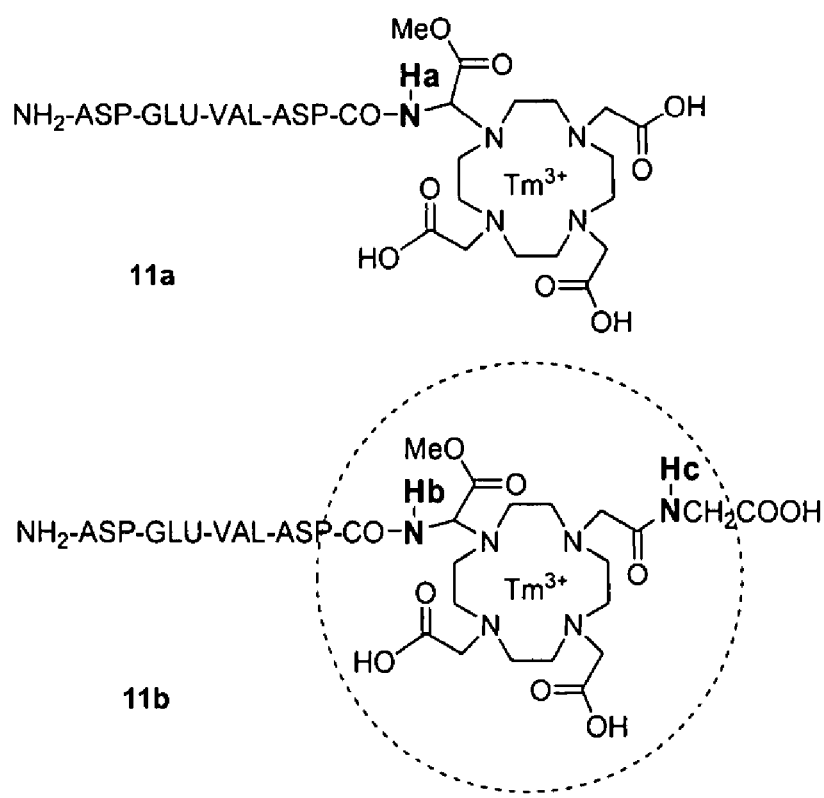
FIG. 4 illustrates the close proximity between one or more amide groups to the lanthanide ion. The peptide Asp-Glu-Val-Asp corresponds to SEQ ID NO: 1.

Selective radio frequency irradiation at −51 ppm created a 7.8% PARACEST effect from 25 mM of 11a. This PARACEST effect of 11a occurs at the same chemical shift frequency and at a similar signal strength reported for a similar compound, DOTAMGly-$Tm^{3+}$. A similar PARACEST effect of 7.3% was observed from 12 mM of 11b. The PARACEST effects from the two amide hydrogens, Hb and Hc (as shown in FIG. 4), both occurred at −51 ppm and were not distinguishable. To investigate the basis for this similarity, molecular modeling of the DOTA core of 11b was performed with carboxylates constrained to conjugate the $Tm^{3+}$ ion. These results revealed that Hb is positioned 4.1-4.3 angstroms from $Tm^{3+}$, and Hc is positioned 4.9-5.1 angstroms from $Tm^{3+}$. As shown in FIG. 4, the dotted line of the two dimensional schematic is 5.4 angstroms from the lanthanide ion, and is provided as an estimate of the similar proximity of Hb and Hc to the lanthanide ion. The PARACEST effect is proportional to the number of water-exchangeable hydrogens that have the same NMR chemical shift. 11b showed a PARACEST effect that was twice as strong as 11a (on a per molar basis), demonstrating that multiple peptidyl ligands can improve the detection sensitivity of PARACEST imaging contrast agents.

Example synthesis methods using SPPS may be applied to couple peptides to other chelators that are used for molecular imaging. For example, diethylenetriaminetetraacetic acid (DTTA) may be used in place of 1 to couple a peptide to diethylenetriaminepentaacetic acid (DTPA). To couple more than 2 peptides to a molecular imaging contrast agent, 1,4,7, 10-tetraazacyclododecaneacetic acid (DOLA) may be used in place of 1 to couple 3 peptides to DOTA following the scheme to synthesize 10a, or to couple 4 peptides to DOTA following the scheme to synthesize 10b. In addition, diethylenetriamineacetic acid (DT1A) may be used in place of 1 to couple 4 or 5 peptides to DTPA. Larger derivatives of DOTA and DTPA, such as hexaazacyclohexadecane-N,N',N", N''', N'''', N'''''-hexaacetic acid (HEHA) and triethylenetetraaminehexaacetic acid (TTHA), provide opportunities to couple additional peptides to a single molecular imaging agent.

In one example, the peptide-DOTA product (e.g., 10a, 10b) can be used to develop in vivo molecular imaging contrast agents for relaxivity-based MRI. The peptide-DOTA product may be used to chelate $Gd^{3+}$ and the peptide-DOTA product may be used to chelate $Dy^{3+}$. The peptide-DOTA product (e.g., 10a, 10b) may also be used to develop molecular imaging contrast agents for nuclear imaging. 10a and 10b may be used to chelate $^{64}Cu$ (53) and 10a and 10b may be used to chelate $^{111}In$.

Figure 5:
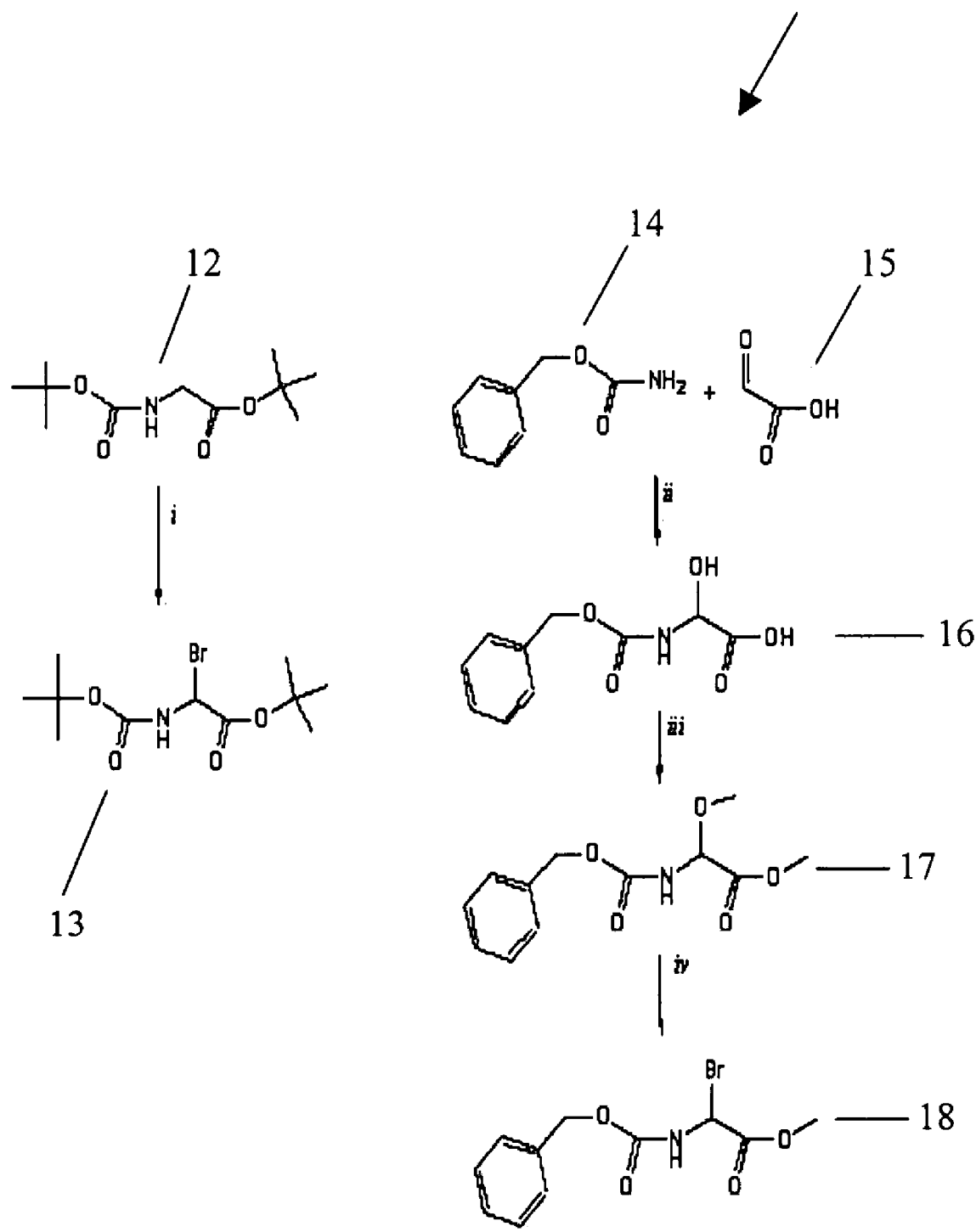
FIG. 5 illustrates two example synthesis pathways for α-brominated glycine templates.

FIG. 5 illustrates two example synthesis pathways for α-brominated glycine templates. α-brominated glycine templates may be employed in a solution phase synthesis of a peptide-based imaging agent or in a solid phase synthesis of a peptide-based imaging agent. Compound 13 was obtained by use of N-bromosuccinimide and filtered UV radiation (254 nm). Compounds 16-18 were synthesized according to a synthetic pathway.

Figure 6:
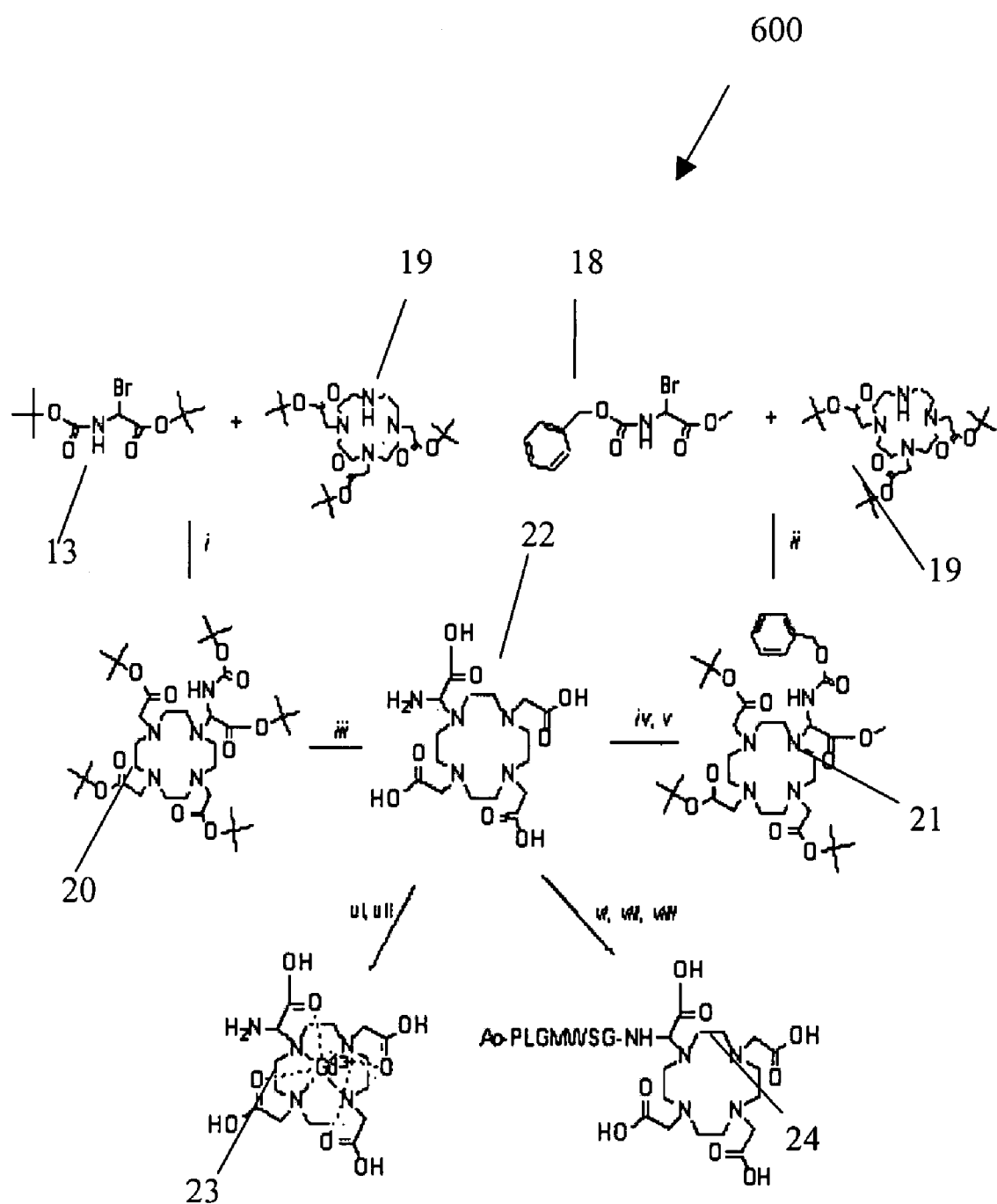
FIG. 6 illustrates the synthesis of α-amino-DOTA derivatives and their coupling to a peptide backbone carboxylate group using a solution phase synthesis method. The peptide PLGMWSG corresponds to SEQ ID NO: 2.

In another example a peptide-based imaging agent can be synthesized using solution phase synthesis. FIG. 6 illustrates the synthesis of α-amino-DOTA derivatives and their coupling to a peptide backbone carboxylate group using a solution phase synthesis method. Compound 20 was synthesized from 13 and 19 and purified with a silica column. The protecting groups of 20 were removed with a cleavage cocktail (95% TFA/2.5% water/2.5% thioanisole) for 30 minutes. The solution was concentrated in vacuo and precipitated with ice-cooled diethyl ether and purified with an amberlite column, yielding 22 as a white solid.

To prepare 21 using solution phase synthesis methods, the compound 18 was coupled to 19 using exhaustive alkylation conditions and purified with a silica column. To remove the CBZ group by hydrogenolysis, 21 was dissolved in 10 mL of absolute ethanol, and 1,4-hexadiene (0.94 mL, 10 mmol) and 10% Pd/C (0.55 g, 10 mmol) were added to the solution. The remaining methyl and tert-butyl protecting groups were removed by hydrolysis using 1 N—NaOH solution. The aqueous solution was lyophilized after purification with an amberlite column, yielding a slightly yellowish solid 22.

To demonstrate the coupling of 22 with the C-terminus of a peptide, a peptide was synthesized with a Wang resin (Fluka, 0.75 mmol/g), HBTU and HOBt coupling agents, and standard Fmoc chemistry protocols using an Applied Biosystems 433A peptide synthesizer. The synthesized peptide sequence was selected to be a substrate for the MMP-2 enzyme. The MMP-2 targeting peptide sequence was SEQ ID No 2 (Ac-Pro-Leu-Gly-Met-Trp-Ser-Gly). The peptide was cleaved from the resin with a 95% TFA/2.5% water/2.5% thioanisole cocktail for 30 minutes. The peptide was purified by crystallization in dichloromethane/diethyl ether and an amberlite column and characterized with a MALDI mass spectrometer (m/z: 811.90 (calcd. 811.91) $[M+Na]^+$). While SEQ ID No 2 was used in the method illustrated in FIG. 6, other sequences can be employed. In one example, a peptide covalently modifiable by an enzyme may be employed (SEQ ID Nos: 1, 2, 10, and 12).

The incorporation of an amino group facilitates the conjugation of 22 to the C-terminus of a peptide backbone. Coupling of 22 to peptide carboxylates expands peptide-DOTA synthesis strategies by complementing methods that couple DOTA to peptide amines. The number of amino groups incorporated into DOTA can be controlled from 1 to 4 by the selection of the macrocyclic starting material, such as cyclen (1,4,7,10-tetraazacyclododecane), DO1A-$^t$Bu, DO2A-$^t$Bu or DO3A-$^t$Bu. To show the application of coupling 22 to the C-terminus of a peptide to synthesize the peptidyl-DOTA structure 24, the synthesized peptide (120 mg, 0.15 mmol) was dissolved in NMP (5 mL) with 63 mg of HBTU and 26 mg of HOBt and stirred for 40 minutes to activate the carboxyl group of the peptide. 22 (80 mg, 0.15 mmol) and TEA (110 µl, 0.75 mmol) in 1 mL of NMP was added slowly at room temperature. The reaction mixture was stirred for 1 hour. After removal of half of the solvents under reduced pressure, the product 24 was precipitated by addition of diethylether (100 mL). The obtained crude product was purified with an amberlite column, yielding product as a white solid (yield 71% by weight) and characterized with a MALDI-MASS spectrometer (m/z: 1190.3 (calcd. 1189.54) $[M+H]^+$).

In one example, the product from the method illustrated in FIG. 6 may be an α-amino-DOTA derivative that conjugates directly to the C-terminus of a peptide using solution phase synthesis methods. In the example, two different glycine templates (e.g., BOC protected, CBZ protected) can be employed via orthogonal protection strategies. One example may include chelating lanthanide ions with DOTA derivatives.

To verify that 22 can serve as a molecular imaging contrast agent, the $T_1$ relaxivity of 23 was measured to assess the efficiency of the chelate to alter $T_1$-weighted MR image contrast. 22 (25.2 mg, 0.06 mmol) was dissolved in water at pH 6 and 60° C., and $GdCl_3$ (150 ul of 0.4 mM solution) was added to this solution and stirred for 1 hour. The pH was adjusted to 8 using 1N NaOH and stirred for 48 hours. The chelation was monitored using a standard Arsenazo III color test. $T_1$ measurements of 23 were conducted at 18° C. and pH 7.1, with samples ranging from 5 mM to 50 mM. The $T_1$ inversion-recovery was examined with a 600 MHz NMR spectrometer. The measured relaxivity was 4.83 $mM^{-1}$ $sec^{-1}$. The relaxivity of $Gd^{3+}$-DOTA that is used in clinical MRI studies is 3.83 m $mM^{-1}$ $sec^{-1}$.

EXAMPLES

The following examples are provided to illustrate the methods of aspects of the invention, and are not to be construed as limiting the invention in any manner.

Example 1

Solid Phase Peptide Synthesis (SPPS)

A. General Methods

Reactions were carried out under argon atmosphere. Methylene chloride (MC) and carbon tetrachloride ($CCl_4$) were freshly distilled over phosphorous pentoxide ($P_2O_5$). Acetonitrile (ACN) was distilled over barium oxide (BaO). The peptide synthesis reagents Fluorenylmethyloxycarbonyl (Fmoc) protected amino acids, N-hydroxybenzotriazole (HOBt), 2-(1H-benzotriazole-1-yl)-1,1,3,3-tetramethyluronium hexafluorophosphate (HBTU), acetic anhydride ($Ac_2O$), piperidine, triethylamine (TEA), N,N-diisopropylethylamine (DIEA), N,N-dimethylformamide (DMF) and N-methylpyrrolidone (NMP) were acquired. The 1,4,7,10-tetraazacyclododecane-N,N',N"-tri(tert-butylacetate) (DO3A-tBu) and other reagents were acquired. Peptides were synthesized using a Wang resin and Fmoc chemistry methods with HOBt and HBTU as coupling agents. The efficiencies of coupling amino acid residues were checked with Kaiser's ninhydrin test. The starting resin had 1.0 mmol/g of hydroxyl groups and the scale of the peptide synthesis was calculated based on the substitution ratio of the resin. The loading efficiencies of the Fmoc-compounds and the amine content of the resin were quantitatively analyzed with UV/Vis/Fluorescence spectroscopy using a Molecular Devices SpectraMax M2 spectrophotometer. IR spectroscopy was used to analyze the functional groups on the resin using an ABB BOMEM MB-104 spectrophotometer operating from 600 to 4000 $cm^{-1}$. To analyze the peptides and the peptide-DOTA amide final product, HPLC was used with a Grace Vydac OD-300 C-18 reverse phase analytical column and a PerkinElmer Series 200 HPLC pump and UV detector operating at 222 nm. The lanthanide complexation reaction between peptide-DOTA amide and $TmCl_3$ was evaluated with an Arsenazo III solution color test. $^1H$ and $^{13}C$ spectra were measured with a Varian Gemini 300 MHz NMR spectrometer and Varian Inova 600 MHz NMR spectrometer using $CDCl_3$ and DMSO-$d_6$ as solvents depending on solubility. PARAmagnetic Chemical Exchange Saturation Transfer (PARACEST) spectra were measured in a solution of 5% $D_2O$ in water using a Varian Inova 600 MHz NMR spectrometer. A series of 1D NMR spectra of the water signal were acquired with a selective saturation in 1 ppm increments between 100 ppm and −100 ppm, and selective saturation was performed with a continuous wave pulse applied for 4 seconds at 31 µT. Analytical thin layer chromatography was performed on Merck silica gel 60 F254 plates. Compounds were visualized using a UV lamp operating at 254 nm, an iodine chamber and ninhydrin solution. High resolution mass spectral analyses were performed with Bruker Daltonics Esquire HCT mass spectrometer and a Bruker BIFLEX III MALDI-TOF mass spectrometer. Molecular modeling was accomplished using InsightII with the Discover-3 (Molecular Simulations Inc.)

B. Synthesis of 4,7,10-tri(t-butylacetate)-1-fluorenylmethoxycarbonyl-1,4,7,10-tetraazacyclododecane (Fmoc-DO3A-tBu)

To a solution of compound 1 (2.57 g, 5 mmol) in 10 mL of acetonitrile, activated zinc dust was added in small portions until the reaction mixture attained neutral pH. A solution of Fmoc-Cl (1.35 g, 5 mmol, 1 eq.) in 5 mL of ACN and zinc dust (325 mg, 5 mmol, 1 eq.) was added to the reaction mixture in one portion and the reaction mixture was stirred at room temperature for 20 minutes. The progress of the reaction was monitored by TLC($CHCl_3$/MeOH=1/1, Rf=0.75). The reaction mixture was filtered and dried in vacuo, yielding 3.32 g of white solid (yield 90%): $^1H$ NMR (600 MHz, DMSO-$d_6$) δ 1.47 (s, 27H), 2.50 (s, 8H), 2.71 (t, 4H), 2.79 (t, 4H), 3.39 (s, 6H), 5.15 (t, 1H), 6.29 (d, 2H), 7.42 (t, 2H), 7.47 (t, 2H), 7.63 (d, 2H), 7.84 (d, 2H), $^{13}C$ (125 MHz, DMSO-$d_6$) δ 170.61, 153.83, 135.59, 135.36, 129.47, 127.23, 123.88, 121.36, 119.99, 81.22, 65.88, 55.14, 53.53, 50.48, 48.44, 47.10, 27.75, MALDI-Mass m/z (calc. 736.94): 737.96 $[M+H]^+$

C. Synthesis of 4,7,10-tri(carboxymethyl)-1-fluorenylmethoxycarbonyl-1,4,7,10-tetraazacyclododecane (Fmoc-DO3A)

2.94 g (4 mmol) of 2 was dissolved in 5 mL of 75% TFA in MC and treated for 40 minutes. The reaction was traced by TLC (chloroform/methanol=1.1, Rf=0.22). The solution was dried under reduced pressure. The remaining solid was re-dissolved in MC and precipitated with diethyl ether. The precipitated solid was filtered and dried in vacuo, yielding 1.70 g (3.0 mmol, yield 75%): $^1H$ NMR (600 MHz, DMSO-$d_6$) δ 3.05 (s, 4H), 3.20 (s, 4H), 3.45 (t, 4H), 3.62 (t, 4H), 3.60 (s, 6H), 4.25 (t, 1H), 4.55 (d, 2H), 7.35 (t, 2H), 7.42 (t, 2H), 7.65 (d, 2H), 7.94 (d, 2H), $^{13}C$ (125 MHz, DMSO-$d_6$) δ 174.21, 155.44, 143.85, 140.63, 127.08, 125.07, 120.01, 67.24, 54.30, 51.88, 50.65, 48.68, 45.79, MALDI-Mass m/z (calc. 568.62): 569.64 $[M+H]^+$.

D. Coupling of Fmoc-DO3A to a Resin

Fmoc-DO3A 3 was then coupled on the resin illustrated as elements 5a and 5b in FIG. 1. The Wang resin 4a (substitution level=1 mmol/g) was used after complete drying. Compound 3 (1.14 g, 2 mmol), HBTU (2.5 g, 6.6 mmol, 3.3 eq.) and HOBt (1.0 g, 6.6 mmol, 3.3 eq.) were dissolved in 30 mL of NMP for 40 minutes to activate carboxylates, and the solution was added to the peptide reaction vessel containing the resin. TEA (1.82 mL, 13 eq.) was added and the reaction was continued for 12 hours. During the reaction, resin was sampled for uncoupled amines using Kaiser's test. After filtration, the resin was dispersed in a solution of tert-butyl alcohol (t-BuOH, 1.48 g, 20 mmol, 20 eq.) in 20 mL of NMP and the reaction was continued for 1 hour. The resin was washed and dried in vacuo. To prepare element 5b, 1.3 g (substitution level=0.78 mmol/g) of element 4b was treated with element 3 following the same synthetic method as for element 4a.

E. Fmoc Titration

The Fmoc concentration on the resin was measured. Fmoc amino acyl resins (4~8 mg) were shaken or stirred in piperidine-DMF (3:7) (0.5 mL) for 30 min, after which MeOH (6.5 mL) was added and the resin was allowed to settle. The resultant fulvene-piperidine adduct had UV absorption maxima at 267 nm (ϵ=17,500$M^{-1}cm^{-1}$), 290 nm (ϵ=5800$M^{-1}cm^{-1}$), and 301 nm (ϵ=7800$M^{-1}cm^{-1}$). For reference, a piperidine-DMF-MeOH solution (0.3:0.7:39) was prepared. Spectrophotometric analysis was carried out at 301 nm, with comparison to a free Fmoc amino acid (Fmoc-Ala) of known concentration treated under identical conditions.

F. Synthesis of Methyl N-(Benzyloxycarbonyl)-α-bromoglycinate

Phosphorous tribromide (8.2 g, 30 mmol, 3 eq.) was added to a suspension of methyl N-(Benzyloycarbonyl)-α-methoxyglycinate (2.51 g, 10 mmol) in carbon tetrachloride (10 mL) under an argon atmosphere. The reaction mixture was stirred at room temperature for 7 days. The reaction solution was then concentrated in vacuo and triturated with dry n-hexane (100 mL) for 24 hrs. The reaction mixture was then filtered, yielding a white solid (75% to quantitative yield measured by weight): $^1H$ NMR (300 MHz, $CDCl_3$) δ 3.80 (s, 3H), 5.22 (s, 2H), 6.20 and 6.45 (split, 1H), 7.55 (s, 5H); $^{13}C$ (125 MHz, DMSO-$d_6$) δ 170.71, 156.07, 137.37, 129.03, 128.57, 128.53, 73.78, 66.25; MS-ESI m/z (calc. 302.99): 304.07 $[M+H]^+$.

G. Coupling of 13 on a Resin

Element 5a (2.22 g, substitution level=0.45 mmol/g) and element 5b (2.13 g, substitution level=0.47 mmol/g) were treated with 20% piperidine for 30 minutes and sequentially washed with NMP, MC, acetone, and acetonitrile. The resin was transferred to a flask with element 13 (0.6 g, 2 mmol, 4.3 eq.) and $K_2CO_3$ (1.66 g, 12 mmol, 25.5 eq.) in dry acetonitrile (100 mL). The solution was stirred and heated to 70° C. for 6 hours in anhydrous conditions. After the solution was filtered, the resin was sequentially washed with 50% MeOH in water, MeOH, and MC, and then dried in vacuo.

H. Cleavage of CBZ Group from the Resin

In each of 3 flasks, 0.20 g (0.1 mmol) of element 7a was dispersed and swelled in MC (5 mL) for 1 hr and cooled to −78° C. $Et_2AlCl$ was transferred into each flask with an air-tight syringe in 1, 2 and 5 eq. and the mixture was stirred for 15 min. 2, 4, and 10 eq. of thioanisole (the molar ratio of $Et_2AlCl$:thioanisole was fixed at 1:2) was added to each flask and portions of the resin were extracted after 5, 15, 30 and 60 minutes of cleavage-reaction time. The sampled resin was washed with MC and titrated with picric acid. To account for tertiary amines on the cyclen ring, a CBZ protected resin was treated and compared as a reference. CBZ cleavage was performed with conditions of 1 eq. of 33% $Et_2AlCl$ in thioanisole for 20 minutes at −78° C.

I. Peptide Synthesis 1.63 g (0.5 mmole) of element 8a was used to synthesize peptide 9a using SPPS methods. Fmoc-Asp(O$^t$Bu)-OH (0.2 g, 0.5 mmol), Fmoc-Val-OH (0.17 g, 0.5 mmol) and Fmoc-Glu(O$^t$Bu)-OH (0.23 g, 0.5 mmol) were used as building amino acids and HBTU (0.19 g, 0.5 mmol) and HOBt (73 mg, 0.5 mmol) were used as coupling agents. Freshly distilled TEA (140 μL, 1 mmol) was used as a base in 70 mL of NMP. 20% piperidine in NMP was used to cleave the Fmoc groups on the resin, after which 1 equivalent of an amino acid was reacted with the resin-bound peptide-DOTA amine. This coupling was repeated with a second reaction that was not preceded with Fmoc deprotection, in order to follow a double-coupling SPPS strategy, which yielded 1.94 g of 9a (calc. 1.97 g, yield 93%). Using the same procedure, 0.42 g (0.14 mmole) of element 8b was treated to synthesize 0.50 g of peptide 9b (calc. 0.52 g, yield 90%).

J. Peptide Cleavage from the Resin

After the peptide synthesis, the Fmoc group of peptide 9a (0.55 g, 0.2 mmole) was removed from the resin and element 9a was cleaved from the resin with a 95% TFA/2.5% water/2.5% thioanisole cocktail for 40 minutes. After removing solvents, the product was washed with diethylether and dried in vacuo. The final product was purified with an amberlite column, yielding 150 mg (0.17 mmol, yield 85%). Following the same procedure, 0.29 g of peptide 9b (0.1 mmole) was used to obtain 87 mg of element 10b (92 μmole, yield 92%).

The obtained products 10a and 10b were characterized by MALDI-MASS (10a m/z (calc. 891.88): 892.89 [M+H]$^+$, 914.89 [M+Na]$^+$; 10b m/z (calc. 948.93): 949.94 [M+H]$^+$, 971.95 [M+Na]$^+$) and HPLC (Column: OD300 RP C-18 column, Detector: 222 nm, Flow rate: 1.0 mL/min, Eluent: 0.1% TFA in water/acetonitrile (gradient from 85%/15% to 5%/95% for 30 min; retention time=2.9 min for 10a and 10b).

K. Complexation of $Tm^{3+}$

The compound 10a (100 mg, 0.11 mmol) was dissolved in water (3 mL) at pH 6.5 and 40° C., and $TmCl_3$ (27 mg, 0.1 mmol) in water (0.5 mL) was added drop by drop for 1 hour and adjusted to pH 7.5 with 0.5N NaOH. The solution was stirred for 18 hours at 40° C. and adjusted to pH 7.5 when the pH dropped below 5. The complete complexation was evaluated with an Arsenazo III color test. When the test showed negative results for free lanthanide ions, the reaction mixture was cooled to room temperature. The pH was adjusted to 9 and the residual lanthanide-hydroxide white precipitate was removed by filtration. The solution was freeze dried, yielding quantitative product 11a (MALDI-Mass m/z (calc. 1060.81): 1061.83 [M+H]$^+$, 1083.85 [M+Na]$^+$). 10b was treated with a similar procedure to obtain the final product 11b (MALDI-Mass m/z (calc. 1117.86): 1118.87 [M+H]$^+$, 1140.92 [M+Na]$^+$).

To the extent that the term "includes" or "including" is employed in the detailed description or the claims, it is intended to be inclusive in a manner similar to the term "comprising" as that term is interpreted when employed as a transitional word in a claim. Furthermore, to the extent that the term "or" is employed in the detailed description or claims (e.g., A or B) it is intended to mean "A or B or both". The term "and/or" is used in the same manner, meaning "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

To the extent that the phrase "one or more of, A, B, and C" is employed herein, (e.g., a data store configured to store one or more of, A, B, and C) it is intended to convey the set of possibilities A, B, C, AB, AC, BC, and/or ABC (e.g., the data store may store only A, only B, only C, A&B, A&C, B&C, and/or A&B&C). It is not intended to require one of A, one of B, and one of C. When the applicants intend to indicate "at least one of A, at least one of B, and at least one of C", then the phrasing "at least one of A, at least one of B, and at least one of C" will be employed.

What is claimed is:

1. A SPPS method for synthesizing a peptidyl contrast agent, comprising:
   synthesizing an amino-chelator loaded resin;
   coupling of the amino-chelator loaded resin to the C-terminus of a peptide;
   cleaving the amino-chelator-peptide from a resin; and
   chelating a lanthanide metal to the amino-chelator-peptide.

2. The method of claim 1, where the synthesizing of the amino-chelator loaded resin includes one or more of, coupling a resin to a chelator having an amine protecting group, cleaving the amine protecting group to expose an amine, reacting protected α-brominated glycine and chelator, and cleaving the protecting group.

3. The method of claim 1, the amino-chelator loaded resin being a DOTA loaded resin.

4. The method of claim 1, the amino-chelator loaded resin being a DTPA loaded resin.

5. The method of claim 2, where the amine protecting group is Fmoc.

6. The method of claim 1, where the resin is a Wang resin.

7. The method of claim 1, the peptide being specific to a cell surface receptor.

8. The method of claim 7, the peptide comprising of an amino acid sequence selected from the group consisting of SEQ ID Nos: 3 and 4.

9. The method of claim 1, the peptide being capable of penetrating a cell membrane.

10. The method of claim 9, the peptide comprising of an amino acid sequence selected from the group consisting of SEQ ID Nos: 5, 6, 7 and 8.

11. The method of claim 1, the peptide being capable of non-specifically interacting with the extracellular matrix.

12. The method of claim 1, the peptide being covalently modifiable by an enzyme.

13. The method of claim 12, the peptide comprising of an amino acid sequence selected from the group consisting of SEQ ID Nos: 1, 7, 8, 9, 11, 13, 14, 15, and 16.

14. A SPPS method for synthesizing a peptidyl contrast agent, comprising:
   synthesizing an amino-chelator loaded resin;
   coupling the amino-chelator loaded resin within the backbone of a peptide;
   cleaving the amino-chelator-peptide from a resin; and
   chelating a lanthanide metal to the amino-chelator-peptide.

15. The method of claim 14, where synthesizing of the amino-chelator loaded resin includes one or more of, adding an amine protecting group, coupling DOTA to a resin, adding CBZ-Gly(Br)-Ome, and cleaving CBZ.

16. The method of claim 14, the amino-chelator loaded resin being a DOTA loaded resin.

17. The method of claim 14, the amino-chelator loaded resin being a DTPA loaded resin.

18. The method of claim 15, where the amine protecting group is Fmoc.

19. The method of claim 14, where the resin is a Wang resin.

20. The method of claim 14, the peptide being specific to a cell surface receptor.

21. The method of claim 20, the peptide comprising of an amino acid sequence selected from the group consisting of SEQ ID Nos: 3 and 4.

22. The method of claim 14, the peptide being capable of penetrating a cell membrane.

23. The method of claim 22, the peptide comprising of an amino acid sequence selected from the group consisting of SEQ ID Nos: 5, 6, 7, and 8.

24. The method of claim 14, the peptide being capable of non-specifically interacting with the extracellular matrix.

25. The method of claim 14, the peptide being covalently modifiable by an enzyme.

26. The method of claim 25, the peptide comprising of an amino acid sequence selected from the group consisting of SEQ ID Nos: 1, 7, 8, 9, 11, 13, 14, 15, and 16.

* * * * *